(12) United States Patent
Fifolt et al.

(10) Patent No.: US 7,889,069 B2
(45) Date of Patent: Feb. 15, 2011

(54) WIRELESS PATIENT MONITORING SYSTEM

(75) Inventors: Douglas A. Fifolt, Wrentham, MA (US); Miki Rosenberg, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 15 days.

(21) Appl. No.: 11/097,499

(22) Filed: Apr. 1, 2005

(65) Prior Publication Data
US 2006/0220839 A1 Oct. 5, 2006

(51) Int. Cl.
*G08B 1/08* (2006.01)
(52) U.S. Cl. .......................... 340/539.12; 340/539.11; 340/573.1; 600/300
(58) Field of Classification Search ............ 340/539.12, 340/539.11, 539.13, 573.1, 573.4; 600/300, 600/301
See application file for complete search history.

(56) References Cited

U.S. PATENT DOCUMENTS

| | | | |
|---|---|---|---|
| 4,519,401 A | 5/1985 | Ko | |
| 5,252,962 A | 10/1993 | Urbas | |
| 5,917,425 A * | 6/1999 | Crimmins et al. | 340/825.49 |
| 6,533,733 B1 * | 3/2003 | Ericson et al. | 600/561 |
| 6,731,976 B2 | 5/2004 | Penn | |
| 6,871,211 B2 * | 3/2005 | Labounty et al. | 709/203 |
| 7,024,245 B2 * | 4/2006 | Lebel et al. | 607/32 |
| 7,034,690 B2 * | 4/2006 | Chaco | 340/573.1 |
| 7,044,911 B2 * | 5/2006 | Drinan et al. | 600/300 |
| 2002/0051221 A1 * | 5/2002 | Wakabayashi | 358/402 |
| 2003/0004403 A1 | 1/2003 | Drinan | |
| 2003/0109905 A1 * | 6/2003 | Mok et al. | 607/60 |
| 2003/0197595 A1 * | 10/2003 | Olson et al. | 340/5.61 |
| 2004/0113771 A1 * | 6/2004 | Ozaki et al. | 340/539.12 |
| 2004/0199056 A1 * | 10/2004 | Husemann et al. | 600/300 |

FOREIGN PATENT DOCUMENTS

| | | |
|---|---|---|
| DE | 4125746 A1 | 2/1992 |
| EP | 830878 A1 | 3/1998 |
| EP | 1057448 A1 | 12/2000 |

* cited by examiner

*Primary Examiner*—George A Bugg
*Assistant Examiner*—Hongmin Fan (57) ABSTRACT

A device and method for monitoring a patient having a sensing device taking sensor data continuously and a transmitter located on the patient and internally powered. The transmitter is normally in a power-down state and powered-up for transmitting the sensor data. A receiver is located remote from the patient and receives the sensor data transmitted wirelessly from the transmitter. The transmission is typically a burst and can also be initiated on a command. For the burst, the sensor data is accumulated over a first period. The transmitter can transmit the sensor data over a second period of time. The second period of time is shorter than the first period of time. Once the transmission is complete, transmitter can be powered down. A further step displays the sensor data at the receiver in pseudo real-time. The display is shifted by a sum of the first and the second period of time.

30 Claims, 4 Drawing Sheets

WIRELESS PATIENT MONITORING SYSTEM

BACKGROUND OF THE INVENTION

1. Field of the Invention

This invention relates to a system and method for measuring, storing and communicating sensor readings from a patient to a central system for display and analysis.

2. Discussion of the Related Art

For certain medical conditions, such as head trauma, it is necessary to place sensors on and in a patient to take continuous sensor readings. One shortcoming of the prior art is the need to wire the sensors to receiving and recording units located near the patient. The wires, especially leading to implanted sensors, cause difficulty for caregivers to move and treat the patient, both in and out of bed. In response, wireless sensor systems were developed that record the sensor data and do not tether the patient to wired receivers. The sensor data is transmitted wirelessly to the receiver. However, continuous wireless data transmission draws a significant amount of power. Since the sensors are wireless, they must rely on battery power and the continuous wireless transmission shortens the battery life and thus the operational life of the sensor.

To overcome some of the above shortcomings, U.S. Pat. No. 4,519,401 to Ko et al. ("Ko") discloses a minimized "pulse" power scheme wherein the sensors and transmitters are placed in a low power cycle when readings are not being taken and then pulse powered up to take a sensor reading and transmit it to a receiver. This power conservation scheme is useful for sensor readings that are only taken at intervals and not continuously. Continuous data sampling would defeat Ko's pulse power scheme, as the sensors and transmitter can never power down.

U.S. Pat. No. 6,533,733 to Ericson et al. ("Ericson") discloses a sensing system wherein the sensor readings are continuously read and stored. The stored data is then periodically transmitted to a receiver. The sensors are continuously powered and transmitter is also continuously powered and draws additional power during power transmission. Ericson realizes that this system is power consumptive and solves the problem by using a combination of power supplies. Ericson is silent regarding powering down the system and Ericson's system could not take continuous readings without constant power. Further, since Ericson's sensor data is stored, the sensor readings are not resented to the caregiver in approximately real-time. Thus, there is a time lag between when the sensor data is taken and displayed. Ericson compensates for this lag by providing the sensor controller with an alarm function to notify a caregiver of an anomalous sensor reading.

U.S. Pat. No. 6,731,976 to Penn et al. ("Penn") discloses a passive sensing system wherein sensor readings are taken and transmitted only when powered externally. The sensing and transmission only last as long as the external power is supplied. This embodiment provides "real-time" sensor data but only while the system is externally powered. Further, Penn discloses an embodiment of providing a power supply for the system but, as Ericson does, Penn takes and stores the sensor data but does not disclose powering down the transmitter to conserve energy. Further, Penn does not disclose how to compensate for the lag between when the sensor data is taken and when it is transmitted.

Thus, there is a need in the art for a sensor system that can take continuous readings and provide the sensor data to a caregiver is pseudo-real-time. Further, there is a need to conserve power of the sensing device and transmitter by powering down the transmitter and transmitting the sensor data only over bursts.

SUMMARY OF INVENTION

A device for monitoring a patient sensor has a sensing device disposed on or in the patient and takes sensor data continuously. A transmitter is located on the patient and internally powered. The transmitter is normally in a power-down state and typically only powered-up for transmitting the sensor data. A first link if formed between the sensing device and the transmitter so the transmitter can receive the sensor data. The first link can include a wired and a wireless link. Further, the wireless transmission can be sent over any known wireless frequencies and utilize any protocols known in the art. A receiver is located remote from the patient and receives the sensor data transmitted wirelessly from the transmitter. The transmission is typically a burst and can also be initiated on a command.

A method of monitoring a patent sensor having the steps of acquiring sensor data from the sensing device and linking the sensor data to the transmitter. The transmitter is powered internally and located on the patient. Typically, the transmitter is powered down in a normal state and powered up to transmit the sensor data from the transmitter to a receiver, which is disposed remote from the transmitter. The transmission can be sent by a burst or upon command.

Another embodiment of the present method includes acquiring sensor data from the sensing device. Typically sensor data is acquired continuously, but can also be taken at intervals. The sensor data is linked to a transmitter by the first communication link and the transmitter is powered internally by a power supply. The sensor data is accumulated over a first period of time which can be a few seconds to a few minutes and, in one embodiment, is a one minute interval. The transmitter can be powered-up and transmitting the sensor data from the transmitter to the receiver over a second period of time. The second period of time is shorter than the first period of time and is typically a factor of shorter. Once the transmission is complete, transmitter can be powered down. A further step displays the sensor data at the receiver in pseudo real-time. The display is shifted by a sum of the first and the second period of time. For example, if the sensor data is accumulated over 1 minute and the burst transmission is 6 seconds, the displayed data is time shifted (or lagged) 66 seconds from real-time.

In a further embodiment, the sensor data can be compressed prior to transmitting the sensor data and then it can be decompressed prior to the displaying the sensor data. Compressing the sensor data can assist in shorting the second period of time and thus shortening the burst period and the lag time.

One or more sensing devices can be linked to a single transmitter. Each sensing device can include a unique sensing device ID which identifies each sensing device. The unique sensing device ID can include the serial number of the sensing device and an identifier to identify the type, model, manufacturer and calibration information of the sensing device. The unique sensing device ID can identify the sensing device for the transmitter. Furthermore, the transmitter can have a unique transmitter ID identifying the transmitter to a receiver and the receiver can also have a unique receiver ID. Receiver ID identifies the receiver to a central server and the sensor data can be encoded/encrypted with the unique receiver ID as outlined above regarding the other unique IDs.

In one embodiment, the receiver is located within 15 feet of the transmitter. The proximity of the receiver to the transmitter can prolong the life of power supply because less power is needed if the transmission is over a short distance. Also, the proximity prevents dropped signals and interference from outside sources.

In another embodiment, the sensor data can be encrypted before it is transmitted wirelessly to prevent unauthorized access or tampering with the sensor data. In a further embodiment, one or both of the unique sensing device ID and the transmitter ID can be used as base keys for encrypting the data. The IDs can be used as a public key and thus either every sensing device's or transmitter's sensor data can be uniquely encrypted.

Further to the above, the first link can include a power link to provide power to the sensing device from the transmitter. The receiver can send a confirmation signal to the transmitter to acknowledging receipt of the sensor data. The confirmation signal is a safety feature to assure that the sensor data is received by the receiver.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PREFERRED EMBODIMENTS

Figure 1:
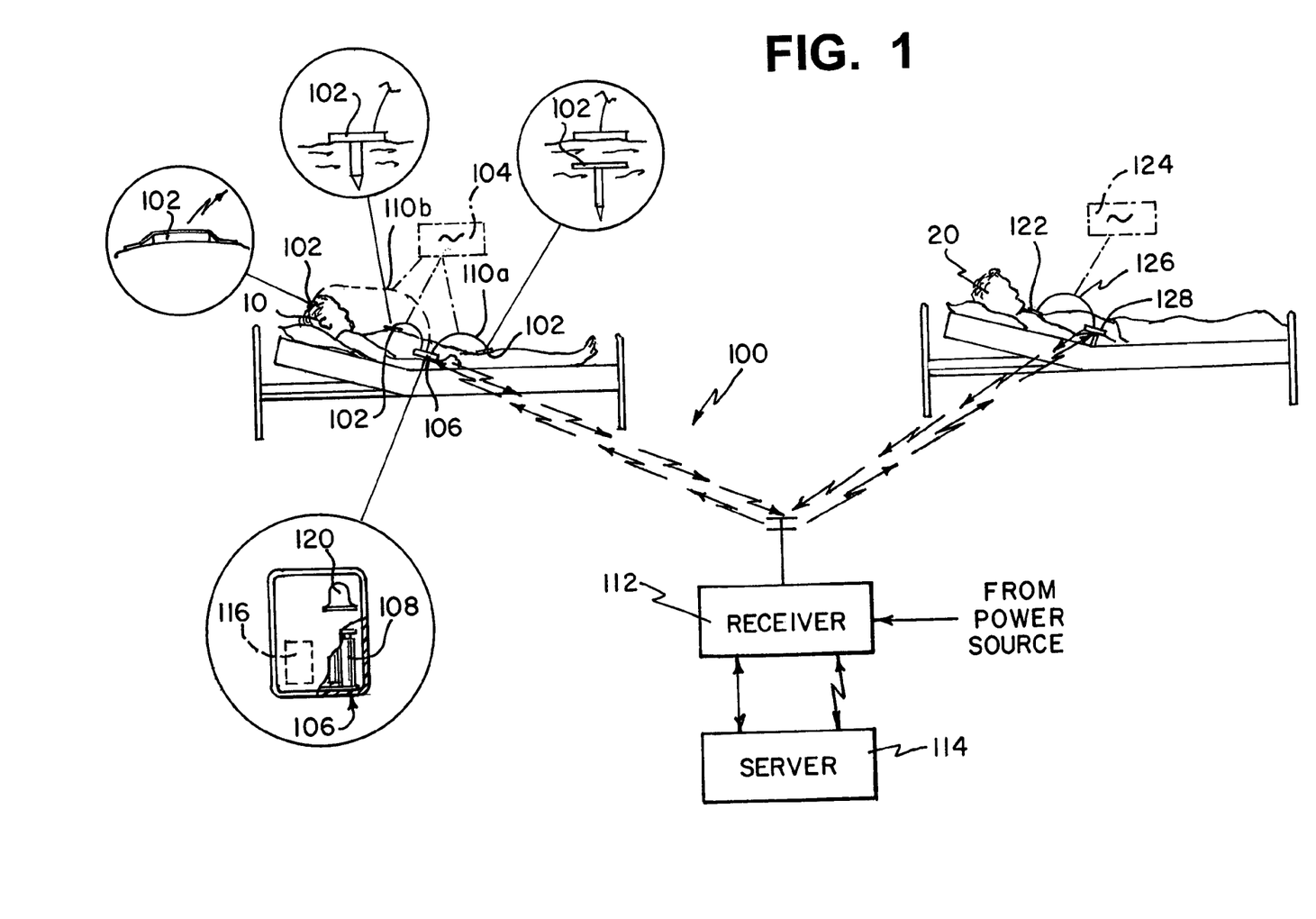
FIG. 1 is schematic diagram of the system of the present invention.

Referring to FIG. 1, a system 100 for monitoring a patient sensor is illustrated. The system 100 includes a sensing device 102 disposed on the surface of or implanted in the patient 10 that takes sensor data 104. The sensing device can be disposed or implanted anywhere on the patient 10, including implanted in the patient's brain. Sensing device 102 can be any medical sensing device, including a pressure sensor, an oxygen sensor, neural impulse sensor, temperature sensor, pH sensor, an electroencephalogram and a fetal heart monitor. The sensing device 102 can collect sensor data 104 over many different time periods. Sensor data 104 can be collected continuously, over either a predetermined or random interval, or upon a command issued from a caregiver. Sensing device 102 can be powered internally by, for example, disposable batteries, rechargeable batteries, or a capacitive device capable of storing energy transmitted through an inductive power coupling or directly through the inductive power coupling.

Sensing device 102 transmits the sensor data 104 to a transmitter 106 located outside the patient 10. The transmitter 106 is typically located on or very close to the patient 10 but not implanted in the patient 10. Typically, transmitter 106 can be strapped to the nearest appendage or adhered to the patient's skin. Transmitter 106 is internally powered by power supply 108. Power supply 108 can be, for example disposable batteries, rechargeable batteries, or a capacitive device capable of storing energy transmitted through an inductive power coupling.

The transmitter 106 receives the sensor data 104 over a first link 110 between the sensing device 102 and the transmitter 106. The first link 110 can be a wired 110a or a wireless link 110b. If the first link 110 is wired link 110a, the transmitter 106 can have multiple leads or ports to accept one or more wired links. The leads and ports can be any type known in the art to transmit at least analogue or digital data to allow the transmission of sensor data 104 to the transmitter 106. If the first link 110 is a wireless link 110b, the transmission can be sent over any known wireless frequencies and utilize any protocols known in the art. Further, wireless link 110b can be transmitted inductively by using the patient's body at the antenna.

Further, the sensing device 102 and the transmitter 106 can undergo handshake protocols to "introduce" the sensing device 102 to the transmitter 106. The handshake can be performed automatically upon the powering up or the plugging in of either the sensing device 102 or the transmitter 106. Alternately, the caregiver can initiate a handshake protocol manually.

One or more sensing devices 102 can be linked to a single transmitter 106. Each sensing device 102 can include a unique sensing device ID which identifies each sensing device 102. The unique sensing device ID can include the serial number of the sensing device 102 and an identifier to identify the type, model, manufacturer and calibration information of the sensing device 102. The unique sensing device ID can identify the sensing device 102 for the transmitter 106. Furthermore, the transmitter 106 can have a unique transmitter ID identifying the transmitter 106 to a receiver 112.

Transmitter 106 transmits the sensor data 104 to receiver 112. Receiver 112 is typically located remote from the patient 10. In one embodiment, the receiver 112 is located within 15 feet of the transmitter. The proximity of the receiver 112 to the transmitter 106 can prolong the life of power supply 108 because less power is needed if the transmission is over a short distance. Also, the proximity prevents dropped signals and interference from outside sources.

The receiver 112 and the transmitter 106 communicate wirelessly, thus allowing patient 10 the freedom to move around and shift position or be moved to aid caregivers activities without disrupting the communications between the two. The communication between the transmitter 106 and the receiver 112 can take place continuously, at an interval, or upon a command. The interval can be either predetermined or random and in one embodiment, the transmitter 106 provides a burst transmission at least every minute. Burst transmissions are used to conserve the power of the transmitter 106. Sending the transmission to the receiver 112 is power consumptive and minimizing the number of transmissions can extend the life of the internal power supply 108. Short interval bursts allow a caregiver to receive nearly real-time sensor data 104 and still conserve the power supply 108.

Further, transmitter 106 can process sensor data 104 through a compression algorithm to compress the data before transmitting it to receiver 112. Compressing sensor data 104 allows for a shorter burst period and assists in reducing the overall power consumption of the transmitter 106 and prolong the life of the power supply 108. Compressed sensor data 104 also conserves storage space on the receiver 112 or server 114. Compressed sensor data 104 can be stored compressed and decompressed for processing or display to the caregiver.

Alternately, the receiver can decompress the sensor data 104 upon receipt and store it decompressed to reduce the wait time for processing or displaying.

Further, the wireless transmission can be sent over any known wireless frequencies and utilize any protocols known in the art. Additionally, the transmitter 106 and the receiver 112 can undergo handshake protocols to "introduce" the transmitter 106 to the receiver 112. The handshake can be performed automatically upon the powering up or the plugging in of either the transmitter 106 or the receiver 112. Alternately, the caregiver can initiate a handshake protocol manually.

In an embodiment, transmitter 106 communicates with receiver 112 utilizing a "burst mode." Burst mode collects and stores sensor data 104 in the transmitter 106 over a set period of time. Typically, the sensor data 104 is compressed to reduce the size of the data packet. Transmitter 106, at the predetermined time, powers up and transmit the stored sensor data 104 in a burst that is typically much, much shorter than the time period over which the sensor data 104 is collected. Transmitter 106 then powers down. The receiver 112 receives and collects the sensor data 104 from the transmitter 106 and decompresses the sensor data 104 back to the original timescale for display or analysis. The receiver 112 displays the data in pseudo real-time—the sensor data 104 is displayed in the same spatial resolution that it was collected with but delayed from real-time by the length of the time period over which it was originally collected plus the communications "burst" time. This embodiment allows transmitter 106 to limit the power expenditure overhead of powering on and establishing link 110 by not requiring the transmitter 106 to perform these tasks for each individual sensor reading taken.

The receiver 112 can be powered by any source, but typically is powered externally, i.e. plugged into the nearest electrical outlet. In an embodiment, receiver 112 can be designed as a permanent or semi-permanent device in the patent's room. Utilizing an external power source to power receiver 112 has advantages. Receiver 112 can be active continuously and can perform storage, analysis, and display functions. Receiver 112 can store and accumulate sensor data 104 for an extended period of time and can store sensor data 104 from numerous transmitters 106 and/or patients 10. Receiver 112 can analyze the sensor data 104 and display it for the caregiver. Additionally, an external power supply allows receiver 112 more flexibility in communicating the sensor data 104, analyzed or not, to a central server 114 located remote from the receiver 112.

Receiver 112 and central server 114 can be linked directly or through a network, LAN, WAN, or the Internet. The connection can be wired or wireless using any protocols known in the art. Central server 114 can be remote from the receiver, i.e. in another room, building or state and a patient 10 can be monitored by a caregiver remote from the patient's location.

In an embodiment, central server 114 can be a portable device (e.g. PDA, cell phone, beeper, Blackberry®) or a semi-portable device (laptop and desktop on wheels) that can be carried by the caregiver or kept in proximity to patent 10 so the caregiver can move into proximity with the patient 10 and display the sensor data 104 at, for example, the patient's bedside. Central server 114 can also store, analyze, and display the sensor data 104. In an embodiment, either the receiver 112 or the central server 114 analyzes the data, or receiver 112 can perform basic analysis and central server 114 performs more detailed analysis if required.

Receiver 112 can also send notifications to central server 114 in response to a number of preset or programmed conditions. For example, if the sensor data 104 shows that there is a critical condition (e.g. the patient's heart stops beating) a notification can be sent (e.g. messaging a pager, ringing a cell phone) notifying the caregiver of the critical condition. As described below, the caregiver can then issue remote instructions to further monitor the patient 10.

If the receiver 112 and the central server 114 communicate wirelessly, all the protocols, handshake procedures and frequencies described above can be used here as described above.

In an embodiment, sensor data 104 can be encoded with the unique sensing device ID and the encoded sensor data is transmitted to the receiver 112 and to the central server 114. Using the unique sensing device ID can identify the specific sensor and thus the specific patient 10. This can help the organization of the sensor data 104 when stored and can assist in the search and retrieval of the sensor data 104 at a later time. Further, sensor data 104 can be encoded with the unique transmitter ID alone or in combination with the unique sensing device ID. The unique transmitter ID can further assist in storage, searching and retrieval.

In one embodiment, the sensor data 104 can be encrypted before it is transmitted wirelessly to prevent unauthorized access or tampering with the sensor data 104. In a further embodiment, one or both of the unique sensing device ID and the transmitter ID can be used as base keys for encrypting the data. The IDs can be used as a public key and thus either every sensing device's or transmitter's sensor data 104 can be uniquely encrypted.

Further to the above, the first link 110 can include a power link to provide power to the sensing device 102 from the transmitter 106. In this embodiment, sensing device 102 does not have a stand alone power supply. If first link 110 is wired 110a, the power can be transmitted directly to the sensing device 102 along the same wire or a different wire than the sensor data 104 is transmitted. Alternately, the power link can be an induced connection. An induction coil from the transmitter 106 can be placed in proximity to an inductance coil in the sensing device 102 to provide power to the sensing device 102. Power supply 108 can provide continuous power or act as a charging station to charge the sensing device 102 on demand. This can be used especially with implanted sensing devices 102. Since transmitter 106 is disposed outside of patient 10, it is easier to recharge power supply 108 and use the transmitter to power sensing device 102.

In an embodiment, transmitter 106 includes a first memory 116 that temporarily stores the sensor data 104 prior to the transmission to the receiver 112. The first memory 116 can be flash RAM or any other type of permanent or removable memory known in the art. First memory 116 can be kept small to allow transmitter 106 to be light weight. Once the sensor data 104 stored on first memory 116 is transmitted to the receiver 112, the sensor data can be erased or overwritten. The overwriting procedure can include overwriting the oldest data first.

Additionally, receiver 112 can include a confirmation signal 118 transmitted from the receiver 112 to the transmitter 106 to acknowledging receipt of the sensor data 104. The confirmation signal 118 is a safety feature to assure that the sensor data 104 is received by the receiver 112. The confirmation signal 118 can also be used as a trigger for the transmitter 106 to erase the first memory 116.

In an embodiment, if the transmitter 106 does not receive the confirmation signal 118, the transmitter 106 can repeat the transmission one or more times until the confirmation signal 118 is received. Also, the transmitter 106 can include an alarm 120 that can send an alarm signal when the confirmation signal 118 is not received once or for a period of time.

Alternately, transmitter 106 can resend the "old" sensor data 104 from the unconfirmed transmission as an add-on to the next transmission of "new" sensor data 104. If the transmitter 106 is set to burst transmissions, adding-on sensor data 104 can lengthen the transmission time but maintains the interval so keep power consumption at a minimum.

In another embodiment, transmitter 106 can be used to communicate with sensing device 102. First link 110 can provide an instruction to the sensing device 102. Examples of instructions can be to turn on/off, change data retrieval intervals, perform a diagnostic test, report power and/or communication status and to take sensor data essentially contemporaneous with the instruction. This allows a caregiver to receive real-time sensor data 104, if the caregiver deems it necessary. The instructions can be originated at the transmitter 106 or at the receiver 112 and/or central server 114 to be transmitted to the transmitter 106 to be relayed to sensing device 104. This configuration allows instructions to originate anywhere the caregiver is located.

Embodiments include using one transmitter 106 per patient 10 and linking multiple sensing devices 104 to the single transmitter 106. A second sensing device 122 can be implanted in the patient 10. The second sensing device 122 takes second sensor data 124 and can include any or all of the features described above for sensing device 102. In a further embodiment, second sensing device can include a unique second sensing device ID. Unique second sensing device ID can be used as above, to identify second sensing device and to encode or encrypt second sensor data 124.

A second link 126 between the second sensing device 122 and the transmitter 106 can be formed similarly to first link 110. Transmitter 106 can receive both sensor data 104 and second sensor data 124. In an embodiment, the transmitter 106 can be programmed to combine the sensor data 104, 124 into a single sensor data file to be transmitted to receiver 112 or can keep the sensor data 104 and the second sensor data 124 separate. To assist in differentiating between the two sensor data, the unique sensing device ID and the unique second sensing device ID can be used to encode and separate the data.

A further embodiment includes using multiple transmitters with one receiver 112. Typically, a second transmitter 128 is linked to a second sensing device 122 implanted in a second patient 20. However, multiple transmitters can be used with the same patient 10, if the positioning of the sensing devices 102 or receiver 112 dictates. As above, second sensing device 122 takes second sensor data 124 and transmits it to second transmitter 128 via second link 126. Second transmitter 128 can include a unique second transmitter ID identifying it. Receiver 112 can receive sensor data 104 and second sensor data 124 from the transmitter 106 and the second transmitter 128, respectively. In an embodiment, the sensor data 104, 124 can be encoded or encrypted using the unique transmitter and second transmitter IDs. Furthermore, if multiple sensing devices are attached to each transmitter, the sensor data can be encoded with both the unique sensing device ID and the unique transmitter ID.

Receiver 112 can also have a unique receiver ID to identify the receiver to the central server 114 and the sensor data 104 can be encoded/encrypted with the unique receiver ID as outlined above regarding the other unique IDs.

Figure 2:
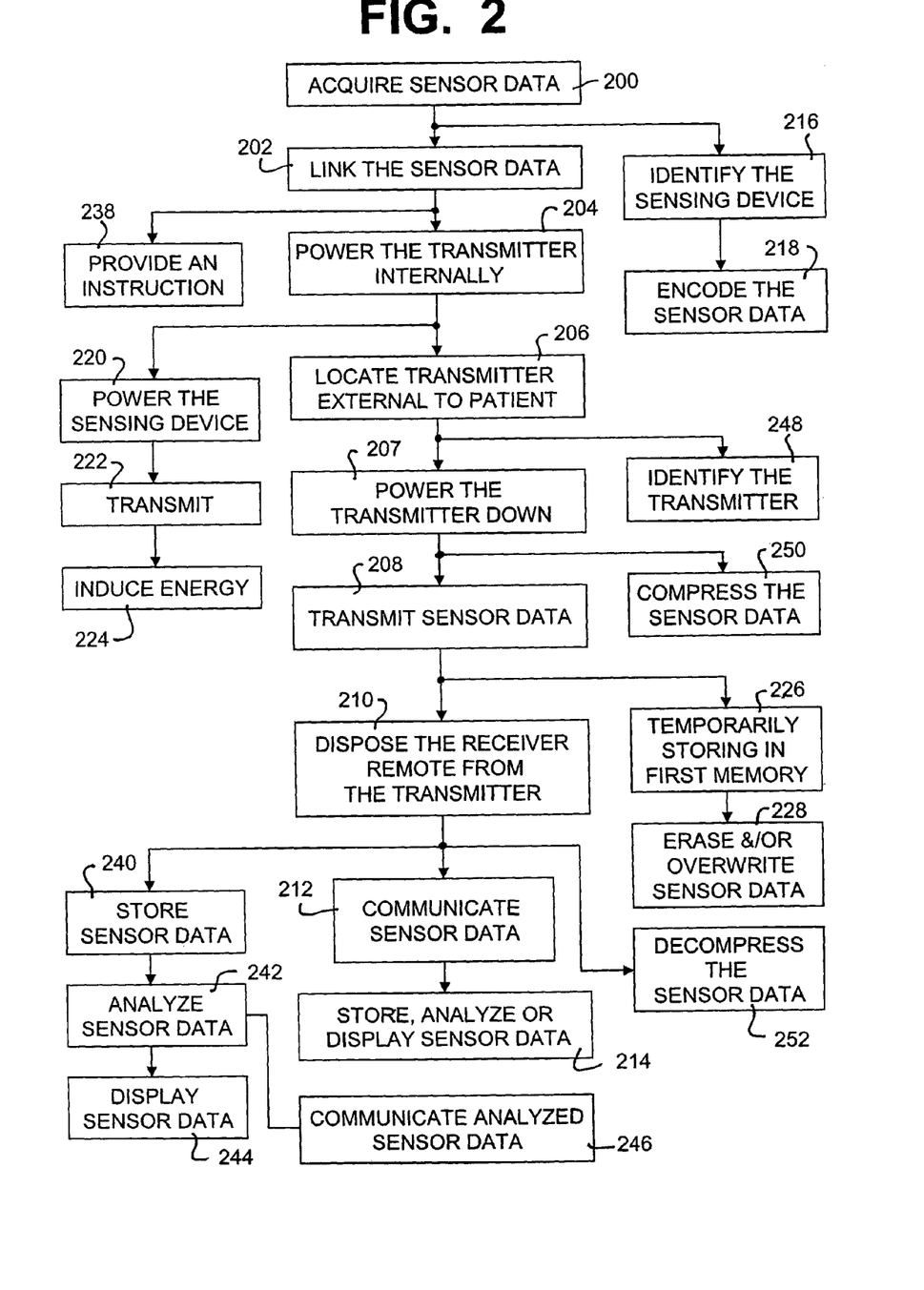
FIG. 2 is a flow chart of an embodiment of a method of the present invention.

FIG. 2 illustrates a method of monitoring a patient sensor. Sensor data 104 can be acquired from sensing device 102 implanted in the patient (step 200) and linked to the transmitter 106 either continuously, at an interval, a burst, or upon command (step 202). The transmitter 106 is powered internally (step 204) and located external to the patient 10 (step 206). Typically, transmitter 106 is in a powered down condition (step 207). The transmitter 106 is powered up and then transmits the sensor data from the transmitter 106 to receiver 112 (step 208) and the receiver 112 is disposed remote from the transmitter 106 (step 210). The sensor data 104 is communicated from the receiver 112 to the central server 114 (step 212) and central server 114 can store, analyze, or display the sensor data 104 (step 214). In an alternate embodiment, the receiver 112 can store, analyze and display the sensor data 104 for an individual patient.

Embodiments include, identifying the sensing device 102 with a unique sensing device ID (step 216) and optionally encoding the sensor data 104 with the unique sensing device ID (Step 218). Further embodiments include powering the sensing device 102 from the transmitter 106 using a power link (step 220) by optionally, transmitting energy over a wire from the transmitter 106 to the sensing device 102 (step 222) or inducing energy through induction coils in the transmitter 106 and the sensing device 102 (step 224). Another embodiment is temporarily storing the sensor data 102 in a first memory 116 prior to the transmitting step (step 226) and erasing and/or overwriting the sensor data after the transmitting step (step 228).

Figure 3:
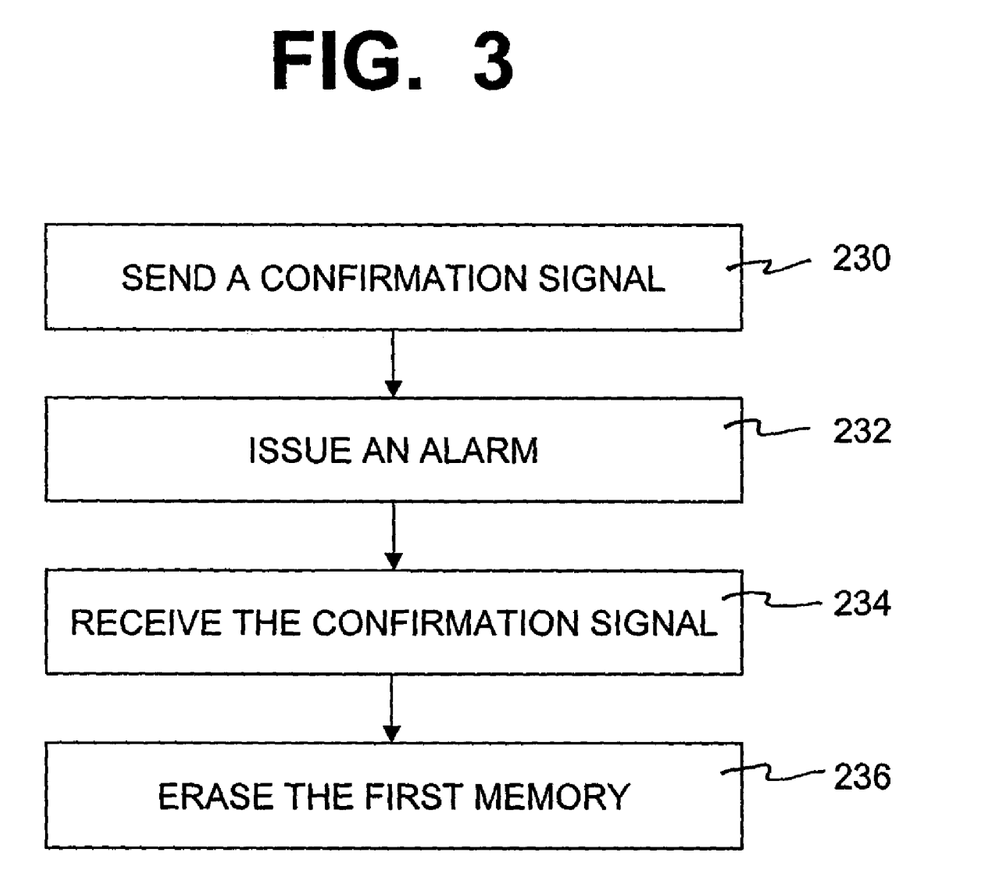
FIG. 3 is a flow chart of another embodiment of a method of the present invention.

Referring to FIG. 3, the method can further include sending a confirmation signal acknowledging receipt of the sensor data 104 (step 230) and issuing an alarm upon failure to receive the confirmation signal (step 232). Additionally, the transmitter 106 can receive the confirmation signal (step 234) and erase the first memory 116 storing the sensor data 104 upon receipt of the confirmation signal (step 236).

Returning to FIG. 2, the transmitter 106 can provide an instruction to the sensing device (step 238). Also, the receiver can optionally, store the sensor data 104 (step 240), analyze the sensor data 104 (step 242) or display the sensor data 104 (step 244). Further, the communicating step above can include communicating the analyzed sensor data 104 to the central server 114 (step 246). Also, the transmitter 106 can be identified with a unique transmitter ID (step 248). In an alternate embodiment, transmitter 106 can compress sensor data 104 (step 250) and receiver 112 can decompress the data (step 252). Alternately, central server 114 can decompress the sensor data.

Figure 4:
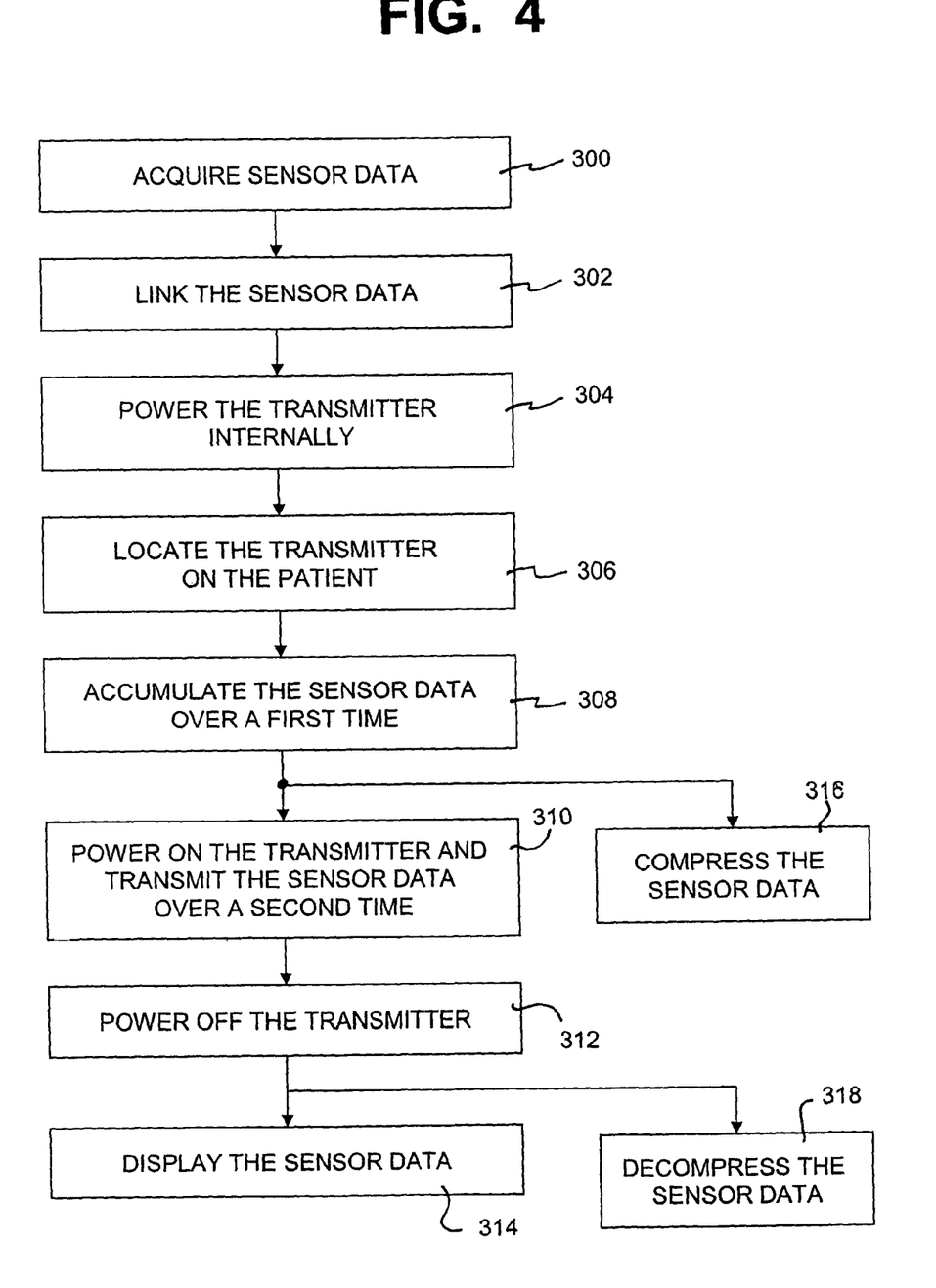
FIG. 4 is a flow chart of a further embodiment of a method of the present invention.

Turning to FIG. 4, another embodiment of the present method is illustrated. The method of monitoring a patent sensor includes acquiring sensor data 104 from a sensing device 102 disposed on the patient 10 (step 300). Typically sensor data 104 is acquired continuously, but can also be taken at intervals. The sensor data can be linked to a transmitter by the first communication link 110 (step 302). The transmitter is powered internally (step 304) by power supply 108 and is typically located on patient 10 (step 306). The sensor data can be accumulated over a first period of time (step 308). The first period of time can be a few seconds to a few minutes and, in one embodiment, is a one minute interval. Transmitter 106 is powered-up and transmits the sensor data 104 from the transmitter 106 to receiver 112 over a second period of time (step 310). The second period of time is shorter than the first period of time and is typically a factor of shorter. Once the transmission is complete, transmitter 106 is powered down (step 312). A further step is displaying the sensor data at the receiver in pseudo real-time (step 314). The display is shifted by a sum of the first and the second period of time. For example, if the sensor data is accumulated over 1 minute and the burst transmission is 6 seconds, the displayed data is time shifted (or lagged) 66 seconds from real-time.

In a further embodiment, the sensor data can be compressed prior to transmitting the sensor data 104 (step 316)

and then it can be decompressed prior to the displaying the sensor data 104 (step 318). Compressing the sensor data 104 can assist in shorting the second period of time and thus shortening the burst period and the lag time. The compression compresses the waveform of the sensor data and the decompression returns the waveform of the sensor data back to its original data.

Further, it is know in the art that any analogue signals can be converted to digital signals before transmission and converted back to analogue signals, if necessary, for display and analysis.

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A device for monitoring a patient, comprising:
   a sensing device disposed at least one of on and in the patient and taking sensor data continuously;
   a transmitter located on the exterior of the patient, internally powered, normally in a power-down state and powered-up for transmitting the sensor data, said transmitter comprising a first memory for temporarily storing sensor data;
   a first link between the sensing device and the transmitter wherein the transmitter receives the sensor data from the sensing device and the first link comprises at least one of a wire and a wireless link;
   a receiver, located remote from the patient, receiving the sensor data transmitted wirelessly from the transmitter and the transmission is at least one of a burst, and upon a command; and
   wherein a confirmation signal is transmitted from the receiver to the transmitter to acknowledge receipt of the sensor data; the confirmation signal instructs the transmitter to erase or overwrite the first memory temporarily storing the sensor data.

2. The device of claim 1, wherein the sensing device comprises a unique sensing device ID and the sensing device is identified by the transmitter using the unique sensing device ID.

3. The device of claim 2, further comprising a central server, located remote from the patient and the receiver, wherein the sensor data is encoded with the unique sensing device ID and the encoded sensor data is transmitted to the receiver and to the central server.

4. The device of claim 1, wherein the first link further comprises a power link to provide power to the sensing device from the transmitter, wherein the power link provides power by at least one of a direct connection and an induced connection.

5. The device of claim 1, wherein the transmitter further comprises an alarm sending an alarm signal upon failure to receive the confirmation signal.

6. The device of claim 1, wherein the transmitter provides an instruction to the sensing device.

7. The device of claim 1, further comprising a central server, located remote from the receiver, receiving the sensor data from the receiver, and at least one of storing, analyzing, and displaying the sensor data and the receiver transmits the sensor data to the central server on at least one of continuously, at an interval, and upon a command.

8. The device of claim 1, wherein the receiver at least one of, stores, analyzes, and displays the sensor data.

9. The device of claim 8, wherein the receiver transmits the analyzed sensor data to a central server.

10. The device of claim 1, wherein the transmitter comprises a unique transmitter ID and the transmitter is identified by the receiver using the unique transmitter ID.

11. The device of claim 10, wherein the sensing device comprises a unique sensing device ID and the sensing device is identified by the transmitter using the unique sensing device ID,
    wherein the sensor data is encoded with the unique sensing device ID and the unique transmitter ID and the encoded sensor data is transmitted to the receiver.

12. The device of claim 1, further comprising:
    a second sensing device implanted in the patient, taking second sensor data at least one of continuously, at an interval, and upon a command, comprising a unique second sensing device ID and the second sensing device is identified by the transmitter using the unique second sensor device ID, wherein the second sensor data is encoded with the unique second sensing device ID; and
    a second link between the second sensing device and the transmitter wherein the transmitter receives the second sensor data from the second sensing device and the second link comprises at least one of one of a wire and a wireless link;
    wherein the sensing device comprises a unique sensing device ID, the sensing device is identified by the transmitter using the unique sensing device ID, and the sensor data is encoded with the unique sensing device ID, and
    wherein the encoded sensor data and the encoded second sensor data are transmitted to the receiver.

13. The device of claim 1, further comprising:
    a second sensing device implanted in a second patient, taking second sensor data at least one of continuously, at an interval, and upon a command;
    a second transmitter located outside the second patient, internally powered, transmitting the second sensor data to the receiver on at least one of continuously, at an interval, and upon a command and comprises a unique second transmitter ID and the second transmitter is identified by the receiver using the unique second transmitter ID; and
    a second link between the second sensing device and the second transmitter wherein the second transmitter receives the second sensor data from the second sensing device and the second link comprises at least one of one of a wire and a wireless link.

14. The device of claim 1, wherein the transmitter compresses the sensor data prior to transmitting to the receiver and wherein the receiver decompresses the compressed sensor data.

15. The device of claim 7, further comprising a notification, sent from the receiver to the central server upon a met condition.

16. The device of claim 1, wherein the transmitter comprises a first memory temporarily storing the sensor data prior to the transmission to the receiver, wherein the sensor data is compressed prior to transmission and decompressed by the receiver.

17. A method of monitoring a patient, comprising the steps of:
acquiring sensor data from a sensing device at least one of on and in the patient;
linking the sensor data to a transmitter by at least one of continuously, at an interval and upon a command, said transmitter having a first memory;
temporarily storing the sensor data in the first memory;
powering the transmitter internally;
locating the transmitter on the exterior of the patient;
powering the transmitter down in a normal state;
powering the transmitter up and transmitting the sensor data stored in the first memory from the transmitter to a receiver by at least one of a burst and upon command;
receiving a confirmation signal sent from the receiver to the transmitter to acknowledge receipt of the sensor data;
erasing or overwriting the sensor data stored in the first memory upon receipt of the confirmation signal; and
disposing the receiver remote from the transmitter.

18. The method of claim 17, further comprising the steps of:
communicating the sensor data from the receiver to a central server; and
at least one of storing, analyzing, and displaying the sensor data at the central server.

19. The method of claim 17, further comprising the steps of:
identifying the sensing device with a unique sensing device ID; and
optionally, encoding the sensor data with the unique sensing device ID.

20. The method of claim 17, further comprising the step of powering the sensing device from the transmitter using a power link, comprising the steps of:
optionally, transmitting energy over a wire from the transmitter to the sensing device; and
optionally, inducing energy through induction coils in the transmitter and the sensing device.

21. The method of claim 17, further comprising the step of issuing an alarm upon failure to receive the confirmation signal.

22. The method of claim 17, further comprising the step of providing an instruction from the transmitter to the sensing device.

23. The method of claim 17, further comprising the step of at least one of:
storing the sensor data at the receiver;
analyzing the sensor data at the receiver; and
displaying the sensor data at the receiver.

24. The method of claim 22, wherein the communicating step includes communicating the analyzed sensor data to a central server.

25. The method of claim 17, further comprising the step of identifying the transmitter with a unique transmitter ID.

26. The method of claim 17, further comprising the step of compressing the sensor data prior to the transmitting step.

27. The method of claim 26, further comprising the step of decompressing the sensor data prior to analysis.

28. The method of claim 18, further comprising the step of communicating a notification to the central server.

29. The method of claim 17, further comprising the steps of:
accumulating the sensor data over a first time;
transmitting the sensor data from the transmitter to the receiver over a second time, shorter than the first time;
powering off the transmitter; and
displaying the sensor data at the receiver in pseudo real-time shifted by a sum of the first and the second times.

30. The method of claim 29, further comprising the steps of:
compressing the sensor data prior to the transmitting step; and
decompressing the sensor data prior to the displaying step.

* * * * *